United States Patent [19]

Giddey et al.

[11] Patent Number: 5,053,219

[45] Date of Patent: Oct. 1, 1991

[54] COSMETIC PRODUCTS CONTAINING MILK CONSTITUENTS

[75] Inventors: Claude Giddey, Geneva; Guy Bunter, Carouge; Dimitri Tzanos, Grand-Lancy, all of Switzerland

[73] Assignee: Rhone-Electra S.A., Geneva, Switzerland

[21] Appl. No.: 397,458

[22] PCT Filed: Dec. 8, 1988

[86] PCT No.: PCT/CH88/00223

§ 371 Date: Aug. 7, 1989

§ 102(e) Date: Aug. 7, 1989

[87] PCT Pub. No.: WO89/05136

PCT Pub. Date: Jun. 15, 1989

[30] Foreign Application Priority Data

Dec. 11, 1987 [CH]   Switzerland ..................... 4839/87-1

[51] Int. Cl.⁵ .......................... A61K 7/07; A61K 7/15; A61K 7/155; A61K 7/02
[52] U.S. Cl. ..................................... 424/63; 424/59; 424/64; 424/70; 252/108; 252/DIG. 5; 252/DIG. 13
[58] Field of Search ....................... 424/70, 59, 63, 64; 514/775; 252/DIG. 13, 108, DIG. 5

[56] References Cited

U.S. PATENT DOCUMENTS 3,644,615  2/1972  Salzberg et al. ...................... 424/70
4,223,018  9/1980  Belle ........................................ 514/2

FOREIGN PATENT DOCUMENTS 46326   2/1982  European Pat. Off. .
1039726  7/1951  France .
85649   7/1919  Switzerland .
701546  12/1953  United Kingdom .
2050160  1/1981  United Kingdom .

OTHER PUBLICATIONS

Chemical Abstracts, vol. 95, 1981, (Columbus, Ohio, U.S.), M. P. Gupta et al.: "Effect of Ions on the Stability of Casein Micelles", voir p. 517, abrege 185704k, & Indian J. Dairy Sci. 1980, 33 (3), 366–73.

*Primary Examiner*—Thurman K. Page
*Assistant Examiner*—Susan S. Rucker
*Attorney, Agent, or Firm*—Cushman, Darby & Cushman

[57] ABSTRACT

A cosmetic or soap product containing natural milk proteins in the form of micelles formed by the addition of calcium to an aqueous solution of casein. These micelles give the product light reflection properties analogous to those produced by the addition of a natural milk.

9 Claims, No Drawings

COSMETIC PRODUCTS CONTAINING MILK CONSTITUENTS

The subject of the present invention is cosmetic and-/or soap products containing substances of milk origin, that is to say ingredients derived from whole or skimmed milk or extracts from milk. The invention is also concerned with the preparation of such products.

The favourable effect of milk or products derived from milk on cosmetic compositions, such as lotions for the skin, hair lotions, shampoos, softening creams, and soaps, is well known, and numerous compositions containing such ingredients have been described in the state of the art.

Thus, the document U.S. Pat. No. 3,959,491 describes cosmetic creams and lotions containing sterilized milk and milk cream. To improve the preservation of such products in storage, this document recommends incorporating into the cosmetic compositions saturated fatty acids, triglyceride esters of saturated fatty acids, stabilising aliphatic diols, sequestering agents and biocidal agents, in particular enzyme denaturants and bactericides. Of course, apart from the preservation agents above, the cosmetics described in this document contain the usual constituents of cosmetics, including perfumes, opacifiers and others.

The document DD-A-112,351 (East Germany) describes cosmetic products containing an active complex derived from milk or whey constituents, in particular non-denatured proteins, vitamins and constituent salts of milk. According to a process for preparation of such an active complex as described in this document, a mass of whey is subjected to concentration under reduced pressure followed by centrifuging and, finally, drying by atomization. For the manufacture of cosmetics, proportions of the order of 10–20% of the active complex such as prepared as described are added to the cosmetics.

The document U.S. Pat. No. 4,460,571 describes a cosmetic on a base of whole or powdered milk which particularly lends itself to topodermic and capillary uses. In this, there are in question fluid compositions, antiseptic and perfumed compositions containing skimmed milk or non-skimmed milk, or containing dissolved powdered milk, and, apart from water and the usual ingredients of such lotions, quite a high proportion of alcohol.

The document GB-A-2,056,854 describes cosmetics, in particular lotions and shampoos, containing, apart from the normal ingredients inherent in such products, very high proportions of milk (40–80%) and, as a stabilising agent, propylene glycol.

The document GB-A-2,051,076 describes a process for preparation of moisturizing agents useful in the field of cosmetics, these agents being derived by fermentation from skimmed milk.

More precisely, this document describes the formation of water soluble casein hydrolysates by the action of lactic ferments and proteases. These hydrolysates, colourless and transparent, are then incorporated, at levels of 0.1 to 10% by weight, into cosmetics, in particular softening lotions for the skin, creams, and soapstuff products, etc., in such a manner as to confer, on these cosmetics, improved properties in respect of softening power, prevention of drying out of the skin, and maintaining its elasticity.

The document GB-A-2,037,160 describes a lyophilised product derived from milk having advantagous cosmetic properties, in particular for moisturizing and softening of the skin along with its regeneration. Such a product contains principally lactose, milk proteins, and water. It is obtained by fermentation of skimmed milk or non-skimmed milk by means of enzymes and milk ferments, in particular pancreatin, pepsin, and the ferments *Lactobacillus bulgaricus* and *Streptococcus thermopilus*. The fermented product is then lyophilised and used, in a mixture, with cosmetic compositions to improve their properties.

The document DE-A-2,623,250 describes cosmetic compositions containing milk. Among these, there are mentioned shampoos, beauty lotions, shaving creams, creams for the skin, etc. All these products have in common, apart from milk and water, surfactant substances, such as alkyl-sulphonates, sulphonated fatty acids, and the salts of tertiary amines, etc. The milk may be present in the form of whole milk, low fat milk, acidified milk, skimmed milk, yogurt, cream, etc. in aqueous form or in a powder. Furthermore, the compositions described may also contain, depending on the use for which they are intended, other ingredients such as lanolin, perfumes, glycerine and other similar products.

The document DE-A-2,650,560 describes cosmetic compositions containing milk in the form of yogurt, this being usable in the fresh state or in a powder. Among such cosmetics, the document mentions liquid and solid products, in particular beauty milks, creams, and aerosols for foams. These compositions contain, apart from yogurt, preserving agents, antioxidants, cheletors, and protease inhibitors.

The document EP-A-46,326 discloses cosmetic compositions applicable to the skin or the hair containing casein in the form of milk or other milk proteins and, more particularly, in the form of whey. These ingredients derived from milk include whey, lactose-free whey, and demineralised whey, and their concentrates prepared by chemical or physical processes, also including the precipitate resulting from neutralisation of the whey, calcium enriched whey, and derivatives of whey resulting from separation of the above-mentioned substances.

Among the cosmetics capable of being improved by the ingredients derived from whey, this document mentions products for care of the skin and the hair, in particular shampoos, dressings, hair lotions, conditioning products, products for permanent waves, dyes, decolourants, body lotions, cold cream, cleansing creams, emollients, detergents, soaps, make-up products, lipsticks, shaving products, sun protecting products, screening products, and depilatories, etc.

In general, for the formulation of such modified cosmetics, there are added to the mixture of the ingredients of the cosmetics, the above-mentioned derivatives of whey, either in the form of aqueous solutions, or in solid form. To ensure the preservation of such cosmetics, the document recommends the addition of inhibiting agents or germicides.

Even though the cosmetics described in the previous art described above show, after modification, by the contribution of milk or of milk derivatives, interesting new properties and undeniable improvements, they are not however without certain disadvantages, among which there may be mentioned:

1) Their composition is often complicated and costly to achieve, not because of the usual cosmetic ingredients, but because of the nature of the milk-derived additives themselves, for example, pre-treatments undergone by these, or the manner of extraction from the natural milk.

2) The storage duration at ambient temperature is often limited and the levels of preservative agents (for example, alcohol) necessary for their preservation is often high, which may compromise, at least in part, the skin softening advantages which result from the presence of the milk-derived constituents.

3) The general aspect of the product is sometimes not very engaging, in particular in regard to a lack of light reflection by the constituents of the composition, a lack which must then be corrected by the incorporation of a pigment, in particular $TiO_2$. It is in effect evident that a product containing substances arising from milk should bring to mind, at first glance, by its appearance and by its colour, that it contains, in effect, such substances.

4) Colour changes. Quite often cosmetic products containing milk have a tendency to yellow with time and, because of this, become unsaleable despite their unchanged intrinsic qualities.

For these various reasons, researches have been undertaken to bring to light new compositions for cosmetic products containing milk derivatives, these compositions really having the appearance of milk or of mixtures containing milk, conserving well in storage, relatively simple to formulate, and displaying, of course, all the recognised advantages of cosmetics formed on a milk base.

These researches have resulted in the products whose definition conforms with the attached claim 1.

It has in effect been observed, surprisingly, that starting from clear solutions of sodium caseinate containing at least one surface-active agent or surfactant, it was possible to obtain, by addition of calcium, in particular soluble salts such as $CaCl_2$ in the pH range indicated, stable milky solutions unmistakeably reminiscent of the appearance of natural milk. Such an operation in fact allows the reformation of milk protein micelles, these being found in the form of calcium phosphocaseinate in a micellar and colloidal suspension. It is interesting to note in this regard that in the absence of a surfactant, such an addition results rather in the precipitation of calcium phosphocaseinate.

The use of industrial casein, either pure or in conjunction with other milk proteins (albumins, globulins, serum proteins) displays the advantages of a product of an essentially constant nature, stable, relatively inexpensive, and practically free of lactose. The effects of yellowing in storage and of alteration that are to be observed in the case of cosmetics containing milk or milk products are in effect, principally due to lactose. It is thus possible, thanks to the use of casein, whose properties and nature remain invariable (within certain limits naturally), to provide cosmetics containing products derived from milk whose composition and performance are stable from one manufacturing run to another, which is extremely difficult to guarantee starting from natural milk.

The colloidal calcium phosphocaseinate solution which is in question here may be used to advantageously modify the majority of cosmetic products modifiable by the addition of milk or of ingredients derived from milk and mentioned in the prior art. In particular, a non-exhaustive list of such products has been given with reference to the document EP-A-46,326. However, the cosmetics which are preferred according to this invention are capillary (hair) products or those for body use such as soaps, shampoos, lotions, creams, and bath products, etc. In a general manner, quantities of milk proteins (in the prescribed form) may be incorporated in such cosmetics and may attain 20% by weight without any major disadvantage in regard to colour, consistency, or stability in storage. Due to the use of purified casein, the addition of germicides and other biocides ma remain minimal.

Among the preferred products of the invention, there may be mentioned products for care of the skin and the hair, in particular products for showers, baths, and shampoos, etc. Such products generally contain surface-active agents (anionic, cationic and non-ionic surfactants, or detergent products), emolliants, and moisturizing agents (fatty materials, fatty acids, protein constituents), biocides (germicides, bactericides. fungicides, etc.) perfumes, blueing agents, and optical opalescents, opacifiers etc.

According to a preferred formula for a shampoo, for example, this contains by weight, the following ingredients: anionic surface-active agents 10–50%, natural fatty acids 0.5–5%, milk-derived proteins 3–15%, calcium ion 0.1–1%, the remainder up to 100% being made up by the water of the solution and at least one additional ingredient selected from among biocides, perfumes, blueing agents, opacifiers, opalescent and iridescent agents, and buffering agents. Preferably, the pH of such a mixture is from 6.5 to 7, and its viscosity is from 3000 to 6000 cP.

Among the surface-active agents suitable for such a formulation, there may be mentioned sodium and ammonium sulphates and sulphonates of fatty alcohols and of polyoxyalkylenes, for example, lauryl sodium sulphate or polyoxyethylene glycol sodium sulphate. However, other surfactants may also suit, for example, non-ionic surfactants.

Among the natural fatty acids, there may be mentioned oleic acid, ricinoleic acid, myristic acid, linoleic acid, and stearic acid.

Among the biocides, there may be mentioned the salts of quaternary amines, p-hydroxybenzoic esters, imidazolidinyl urea, phenoxyethanol, derivatives of isothiazolinone, formaldehyde, and benzoic, salicylic and sorbic acids.

To prepare cosmetics according to the present invention, one will advantageously have recourse to the process defined in claim 6. It may be noted that the term casein or soluble caseinate refers to either sodium, potassium or ammonium caseinate, or acidic casein dissolved in an alkaline medium.

Thus, for example, in the case of the preparation of a shampoo composition such as defined in claim 4, one may operate in the manner defined in claim 7. Preferably $CaCl_2$ is used as calcium salt, for example, in the form of $CaCl_2.2H_2O$; however, other water soluble calcium salts may also be used.

The Examples that follow illustrate the invention.

EXAMPLE 1: Preparation of a shampoo composition.

In 740 g of cold water, 72.1 g of sodium caseinate (AME-100, provided by the Central Union of Swiss Milk Producers) were dispersed, then this mixture was heated to 70° C. in a homogeniser until completely dissolved. Then 120 g of sodium sulphate and of lauryl sulphate (Texapon - Z, supplied by Impag A. G., Zurich) and 24 g of oleic acid were added to the solution.

The temperature was then reduced to 50° C., and 3 g of imidazolidinyl urea and 5 g of phenoxyethyl p-hydroxybenzoate were added; then the pH was adjusted to 6.75 by means of a 20% by weight aqueous KOH solution, and, with vigorous agitation and cooling, 20.5 g of an aqueous solution of 64.8% by weight of $CaCl_2.2H_2O$ were added drop by drop.

The mixture changed from clear to a milky mass of an intense white colour, which was then perfumed by addition of 4 g of a perfume (Freezia, supplied by GIVAUDAN S. A., Geneva). This shampoo composition was tested by the usual means employed for cosmetics and demonstrated an excellent washing power, while still preserving the hair and giving it an excellent gloss.

Storage tests for this shampoo at 40° C. have not shown any tendency towards flocculation or separation of phases. At most a slight lessening in light reflection has been observed, an effect which however disappeared on cooling.

EXAMPLE 2: Preparation of a composition for baths.

The following ingredients were intimately mixed at 70° C. in a homogeniser.

| Ingredients | g |
| --- | --- |
| Water | 717 |
| Sodium caseinate (AME-100) | 162 |
| Texapon-Z | 78 |
| Oleic acid | 38 |
| There was then added, at 50° C. | 5 |
| Phenonip (Nipa. GB) | |

This mixture was called premix A.

A product for baths was then formed at 70° C. by successive addition of the following ingredients (% by weight).

| Ingredients | % |
| --- | --- |
| Water | 6.32 |
| SAG-10 (Silicone antifoam from Union Carbide). | 0.15 |
| Texapon-Z (Henkel) | 8.87 |
| Texapon-N (Henkel) | 37.51 |
| Neo-Purcellin-SE (0/W - 2/066280) (emulsifier supplied by DRAGOCO, Germany) | 2.0 |
| Premix A | 35.0 |
| Euperlan PK-771 (iridescent agent supplied by Henkel, Germany) | 3.0 |
| KOH (7.4% solution) | 0.62 |
| Then after cooling to about 50° C., there are then added: | |
| Phenonip - 100 | 0.2 |
| Biopur - 100 | 0.2 |
| $CaCl_2.2H_2O$ (64.8% solution) | 3.63 |
| Perfume | 2.5 |

The whole was then homogenised at 7000 rpm for 5 mins., which yielded a composition of pH 6.75.

By using the above product, whose appearance is of a constant milky white with iridescent reflections, in water, a very agreeable softening bubble bath was obtained.

EXAMPLE 3: Preparation of a skin cream

In a mixer, 45.6 g of casein were dissolved in 548.8 g of water, the solution was then brought to 70° C. and to it were added, while agitating, 24 g of glycerol. This solution was identified as M-1.

In a mixer (Sovirel type SVS - 295), there were mixed at 70° C., 32 g of Cutina KD - 16 and 24 g of Lanette 0. Then, after 30 mins. of agitation, 80 g of Cetiol V and 8 g of sweet almond oil were added. After agitation for 15 mins. at 70° C., 5.6 g of anhydrous lanolin and 8 g of castor oil were then added. This mix was identified as M-2.

While gently agitating at 70° C., the product M-2 was slowly incorporated into the product M-1. The temperature was then lowered to 50° C., and, while continuously agitating, there were successively added 16 g of Hydroviton, 1 g of lactic acid, 2 ml of a 64.8% calcium chloride solution, 0.8 g of Kathon CG, and 4 g of perfume. The temperature was then lowered to 40° C., and homogenisation at 7000 rpm for 5 mins. was carried out.

A fluid revitalising cream was then obtained, allowing the skin to be softened after a bath and it to be rendered supple and soft, while still giving an agreeable impression of freshness. This cream is suitable for even the most sensitive skins.

We claim:

1. A cosmetic or a soap product having the appearance of natural milk and comprising, other than the usual ingredients of such a product, a surface active agent and at least one substance derived from milk, wherein this substance includes a member selected from the group consisting of casein, and a mixture of casein and other milk proteins, said casein containing no more than 0.1% of lactose, said casein being present, at least in part, in the form of a colloidal and micellar solution of calcium phosphocaseinate at a pH of from 6 to 7.

2. A cosmetic product according to claim 1, characterised in that its content of proteins of milk origin is from 3 to 20% by weight.

3. A cosmetic product according to claim 1, characterised in that it consists of a shampoo containing, by weight: anionic surface-active agent 10–50%, oleic acid 0.5–4%, proteins derived from milk 3–15%, $Ca^{++}$ ion 0.1–1%, the remainder to 100% being formed of water and one or several additional ingredients selected from among biocides, perfumes, blueing agents, opacifiers, and buffering agents.

4. A cosmetic product according to claim 3, characterised in that its viscosity at ambient temperature is from 3000 to 6000 cP.

5. A process for preparing a cosmetic product according to claim 1, characterised in that at least a part of the usual constituent ingredients of the said product are incorporated in a homogeneous manner, these including at least a surface-active agent, a clear aqueous solution of casein or soluble caseinate optionally containing other proteins of milk origin, then a sufficient quantity of calcium ions is added so that at pH 6–7 the soluble caseinate is converted into a micellar colloid of calcium phosphocaseinate, then, if necessary, the remainder of the constituent ingredients of the cosmetic are added.

6. A process according to claim 5, applied to the preparation of a shampoo according to claim 3, characterised in that all or part of the surface-active agent and of the oleic acid are mixed at a temperature of 50°–80° C. with an aqueous solution of sodium caseinate, the greater part or all of the other ingredients with the exception of the $Ca^{++}$ ions are added, then, between 40° and 60° C. and at a pH adjusted to a value between 6 and 7, a concentrated aqueous solution of a water soluble calcium salt is slowly added, which converts the clear solution into a milky solution of high light reflective power.

7. A process according to claim 6, characterised in that the calcium salt is calcium chloride.

8. A cosmetic or a soap product having the appearance of natural milk and comprising, other than the usual ingredients of such a product, a surface active agent and at least one substance derived from milk, wherein this substance includes a member selected from the group consisting of casein, and a mixture of casein and other milk proteins, said casein containing no more than 0.1% of lactose, said casein being present in an effective amount so as to result in said appearance of natural milk and being present, at least in part, in the form of a colloidal and micellar solution of calcium phosphocaseinate at a pH of from 6 to 7.

9. A method for modifying cosmetic products selected from the group consisting of products for care of the skin and the hair, shampoos, dressings, hair lotions, body lotions, cold cream, cleansing creams, emollients, detergents, soaps, make-up products, lipsticks, shaving products, sun screen products and depilatories by giving them an appearance reminiscent of containing natural milk, comprising the steps of incorporating to said cosmetic products at least one surface-active agent, soluble calcium salt and a substance selected from the group consisting of casein, and a mixture of casein and other milk proteins, said casein containing no more than 0.1% of lactose, said casein being present in an effective amount so as to result in said appearance of natural milk and being present, at least in part, in the form of colloidal calcium phosphocaseinate at pH from 6 to 7.

* * * * *